United States Patent [19]
Schaffner et al.

[11] Patent Number: 6,132,993
[45] Date of Patent: Oct. 17, 2000

[54] PROCESS FOR THE PRODUCTION OF AMPHOTERICIN-B INHIBITING PRODUCTION OF AMPHOTERICIN-A

[75] Inventors: Carl P. Schaffner, Trenton; David J. Kientzler, Robbinsville, both of N.J.

[73] Assignee: Rutgers University, Piscataway, N.J.

[21] Appl. No.: 09/083,620

[22] Filed: May 22, 1998

Related U.S. Application Data

[63] Continuation-in-part of application No. 08/514,295, Aug. 11, 1995, abandoned.

[51] Int. Cl.$^7$ ..................................................... C12P 19/62
[52] U.S. Cl. ........................... 435/76; 435/244; 435/119; 435/170
[58] Field of Search .............................. 435/76, 244, 119, 435/170

[56] References Cited

U.S. PATENT DOCUMENTS 2,908,611  10/1959  Dutcher et al. .
2,908,612  10/1959  Dutcher et al. .

OTHER PUBLICATIONS

Gold, W., et al., "Amphotericins A and B, Antifungal Antiobiotics Produced by a Streptomycete, I. In Vitro Studies", *Antibiotics Annual 1955–1956*, 576–578.

Vandeputte, J., et al. "Amphotericins A and B, Antifungal Antibiotics Produced by a Streptomycete, II. The Isolation and Properties of the Crystalline Amphotericins", *Antibiotics Annual 1955–1956*, pp. 587–591.

Mechlinski, W., et al., "Structure and Absolute Configuration of the Polyene Macrolide Antibiotic Amphotericin B", *Tethrahdron Letters*, 1970, No. 44, pp. 3873–3876.

Ganis, P., et al., "Polyene Macrolide Antibiotic Amphotericin B. Crystal Structure of the N–Iodoacetyl Derivative", *The Journal of the American Chemical Society*, 1971, 93:18, pp. 4560–4564.

Linke, H., et al., Production of Amphotericin B–$^{14}$C By *Streptomyces Nodusus* Fermentation, and Preparation of the Amphotericin B–$^{14}$C Methyl–Ester, *The Journal of Antibiotics*, 1974, pp. 155–160.

Sowinski, P., et al., "The Structure of Amphotericin A. I. Mass Spectrometric Analysis of Dodecahydroamphotericin A", *The Journal of Antibiotics*, 1985, vol. XXXVII No. 2, pp. 169–174.

Sowinski, P., et al., "The Structure of Amphotericin A. II. The Complete Structure of the Antibiotic", *The Journal of Antibiotics*, 1985, vol. XXXVIII, No. 2, pp. 175–180.

Liu, Y., Biosynthetic Studies of Amphotericins, Candicidin, and Nystatin by Means of Mutation, *Proc. Natl. Sci., Counc, ROC*, 1984, vol. 8, No. 2, pp. 182–186.

Perlman, D., et al., Preparation of Amphotericin B–$^{14}$C, *Biotechnology and Bioengineering*, vol. VII, pp. 133–137.

Trejo, W.H., et al., *Streptomyces Nodosus* Sp. N., The Amphotericin–Producing Organism, *Journal of Bacteriology*, 1963, vol. 85, pp. 436–439.

Landini, P., et al., Inhibition of bacterial protein synthesis by elongation–factor–Tu–binding artibiotics MDL 62,879 and efrotomycin, *Biochem. J.*, 1992, 283(3), pp. 649–652.

Rahman, M.A., et al., Antibacterial Activity and Inhibition of Protein Synthesis in *Escherichia coli* by Antisene DNA Analogs, *Antisense Research and Development*, 1991, 1(4), pp. 319–327.

Shabas et al, Antibiotiki (MOSC), 22(5), 1977 p. 396–400.

*Primary Examiner*—Irene Marx
*Attorney, Agent, or Firm*—Davidson, Davidson & Kappel, LLC

[57] ABSTRACT

Methods are provided for improving the microbial production of amphotericin B by the selective inhibition of amphotericin A by means of protein synthesis inhibitors.

10 Claims, 8 Drawing Sheets

PROCESS FOR THE PRODUCTION OF AMPHOTERICIN-B INHIBITING PRODUCTION OF AMPHOTERICIN-A

This application is a continuation-in-part of U.S. patent application Ser. No. 08/514,295, filed Aug. 11, 1995, now abandoned.

FIELD OF THE INVENTION

This invention relates to the use of protein synthesis inhibitors during cultivation of amphotericin producing microorganisms to selectively inhibit the co-production of amphotericin A so as to increase the purity of the desired production of amphotericin B.

BACKGROUND OF THE INVENTION

Amphotericin B is the most widely used antifungal antibiotic for the treatment of life-threatening, deep-seated, systemic fungal infections. Although amphotericin B is the preferred antibiotic of choice for the systemic treatment of such life-threatening fungal infections, its use is limited by severe toxicity. Amphotericin B is presently produced by the cultivation of Streptomyces nodosus along with the toxic but substantially less active homolog, amphotericin A, as first described by Gold et al., 1956, Antibiotics Ann. 19955–19956:579–586. However, given the complexity of the synthetic pathway, should other strains of microorganisms be found to produce amphotericin B, it is expected that those new strains will produce amphotericin B by substantially the same pathway as is used by amphotericin B producing strains of Streptomyces.

Streptomyces nodosus is a streptomycete isolated from a soil sample taken from the Orinoco River region of Venezuela and identified as Streptomyces nodosus by Trejo et al., 1963, J. Bacteriol. 88:436–439. The microbial production and isolation of amphotericin B and amphotericin A from Streptomyces nodosus is described by Dutcher et al., U.S. Pat. Nos. 2,908,611 and 2,908,612, respectively, the disclosures of which are incorporated by reference herein in their entireties. Due to the toxic contribution of amphotericin A, which is a substantially less potent antifungal agent, amphotericin B for systemic use must have substantially all or most of the amphotericin A removed in order to achieve an acceptable therapeutic index. For example, amphotericin B for intravenous use must be at least 75% pure and contain no more than 5% amphotericin A (marketed as, e.g., FUNGIZONE, by E. R. Squibb & Sons, Inc.). The level of impurities in amphotericin B preparations depends upon the particular production strain, the cultivation conditions (electrolytes, pH and the like) and upon the purification methods applied to the crude fermentation product.

The structure and absolute configuration of amphotericin B was determined by X-ray crystallography and was reported in 1970 by Mechlinski et al., 1970, Tetrahedron Lett. 44:3873–3876., as shown below.

AMPHOTERICIN B

While the complete absolute configuration of amphotericin A has not been determined, it is very likely that the stereochemistry of amphotericin A is related, if not identical, to that of amphotericin B.

AMPHOTERICIN A

It is now believed that the only difference between these structurally homologous antibiotics is the reduction of the $C_{28}$–$C_{29}$ double bond of the amphotericin B heptaene chromophore, resulting in the formation of the diene and tetraene structures in amphotericin A. Therefore, due to the close homology of these two compounds, the separation of amphotericin B from amphotericin A has heretofore proved to be a time-consuming and expensive chemical process that is often still based essentially upon the methods disclosed by U.S. Pat. Nos. 2,908,611 and 2,908,612, supra.

M. Shabas, et al, in Comparative Study of the Streptomycin Effect on Variation in Levorin and Amphotericin B Producers, Antibiotiki (Mosc.) 22(5), 1977, pp. 396–400, describes a study of the effect of streptomycin in the range of 1 to 6 μg/ml. on the production of amphotericin B. However, the levels of streptomycin used in Shabas are cytotoxic, and would adversely affect the production of both amphotericin A and amphotericin B.

Thus, an improved method for the production of amphotericin B that provides substantially greater purity relative to its amphotericin A content has been long-sought and heretofore unavailable.

OBJECTS OF THE INVENTION

It is therefore an object of the present invention to provide an economical process for producing amphotericin B by the cultivation of amphotericin B producing microorganisms, with a substantially increased purity, by selectively inhibiting the co-production of amphotericin A by such microorganisms.

It is a further object of the present invention to provide a process for selectively inhibiting the production of amphotericin A during the cultivation of amphotericin A producing microorganisms without substantially inhibiting amphotericin B production.

SUMMARY OF THE INVENTION

The invention provides a new process for producing amphotericin B by the cultivation of amphotericin B—producing microorganisms at a higher yield with a substantially reduced co-production of amphotericin A. The process includes the steps of cultivating an amphotericin B producing strain of microorganism in a nutrient medium suitable for the production of amphotericin B, the nutrient medium further comprising a protein synthesis inhibitor in a concentration effective to substantially and selectively inhibit amphotericin A synthesis without substantially inhibiting amphotericin B synthesis. Amphotericin B is then recovered from the medium.

Amphotericin B is preferably produced by Streptomyces microorganisms such as, for example, Streptomyces nodosus. In the method according to the invention, Streptomyces nodosus can be cultivated with a protein synthesis inhibitor that binds to an 80S and a 70S ribosome of Streptomyces nodosus, or preferably with an inhibitor that binds primarily to the 70S ribosome or to one of the components of the 70S ribosome, consisting of, for example, the 16S, 23S, 30S and 50S ribosomal RNA of Streptomyces nodosus.

Further, Streptomyces nodosus can be cultivated with a protein synthesis inhibitor that is an antibiotic effective to selectively inhibit co-production of amphotericin A without substantially impairing Streptomyces nodosus growth or amphotericin B production.

In particular, Streptomyces nodosus can be cultivated with a protein synthesis inhibitor that is an antibiotic such as, e.g., a member of the aminoglycoside group including streptomycin, dihydrostreptomycin, neomycin, paromomycin, kanamycin, gentamicin, tobramycin and amikacin. The protein synthesis inhibitor can also be an antibiotic selected from the group consisting of chloramphenicol, lincomycin, thiostrepton, capreomycin, spectinomycin, chlortetracycline and erythromycin. In a preferred process, Streptomyces nodosus can be cultivated with a protein synthesis inhibitor comprising chloramphenicol or lincomycin.

Also contemplated by the invention for the cultivation of Streptomyces nodosus are elongation factor inhibitors, such as ganefromycin.

Protein synthesis inhibitors may be added to the nutrient medium in one or more doses at various stages of the production process, and in a wide range of concentrations. A preferred total concentration range is up to about 1.0 μg/ml, and is preferably less than 1.0 μg/ml. A particularly preferred total concentration range is from about 0.10 μg/ml to about 0.75 μg/ml. A more preferred total concentration is from about 0.1 μg/ml to about 0.5 μg/ml, and a most preferred total concentration is about 0.4 μg/ml.

For elongation factor inhibitors, such as ganefromycin, a preferred total concentration range is from about 5 to about 25 μg/ml.

By "concentration range" is meant the amount of protein synthesis inhibitor per amount of nutrient medium. By "total concentration range" is meant the amount of protein synthesis inhibitor per amount of nutrient medium after the addition of all doses, including the initial dose and any supplemental doses.

The protein synthesis inhibitors of the invention can be added to the nutrient medium at least once during the time after commencement of cultivation and preferably before amphotericin A begins to accumulate in significant quantities.

Thus, the inhibitor can be added in an initial dose at a time ranging from about 0 to about 100 hours or more after the start of Streptomyces nodosus cultivation, and thereafter may be added in supplemental doses. Preferably, the inhibitor is added in an initial dose at a time ranging from 0 to 48 hours. More preferably, the protein inhibitor is added to the nutrient medium in an initial dose at a time ranging from about 0 to about 24 hours after commencement of Streptomyces nodosus cultivation. Alternatively, the protein inhibitor can be added to the nutrient medium at a time ranging from about 24 to about 100 hours after commencement of Streptomyces nodosus cultivation.

Most preferably, the protein synthesis inhibitor is added to the culture medium in an initial dose at the start of cultivation. One or more supplemental doses of protein synthesis inhibitor may also be added during cultivation to suppress residual amphotericin A expression, as necessary.

Of course, the protein synthesis can be added continuously during all or part of the cultivation process, especially for cultivation cycles that require the repeated or continuous addition of cultivation medium.

BRIEF DESCRIPTION OF THE FIGURES

In order that the disclosure of the invention may be fully appreciated, the following figures are provided, which are in no way intended to limit the scope of the invention.

DETAILED DESCRIPTION OF THE INVENTION

Accordingly, the invention provides a new process for producing amphotericin B by the cultivation of amphotericin B producing strains of microorganisms such as, for example, amphotericin B producing strains of Streptomyces, at a higher purity. This is accomplished by the addition of a low concentration of a protein synthesis inhibitor to the cultivation medium.

Any art-known cultivation technique suitable for cultivation of amphotericin B-production microorganisms may be used. The cultivation may be continuous or continuous flow cultivation or any other methods readily appreciated by the ordinary artisan that are suitable to either the small scale or industrial scale production of amphotericin B. The amphotericin B-producing microorganisms, such as, for example, Streptomyces nodosus, is used to produce amphotericin B with a surprising and unexpected modification of art-known methods, by cultivation in a nutrient medium (see, e.g., U.S. Pat. Nos. 2,908,611 and 2,908,612, cited supra) suitable for the production of amphotericin B where the modification consists of the addition of a protein synthesis inhibitor to the nutrient medium during cultivation, in a concentration effective to substantially and selectively inhibit amphotericin A synthesis without substantially inhibiting amphotericin B synthesis. Amphotericin B is then recovered from the medium.

Streptomyces nodosus strains are readily available, for example, from both academic and commercial sources, such as, for example, The Institute of Microbiology, IMRU No. 3694, Rutgers University, Piscataway, N.J. 08855–0759 or from the American Type Culture Collection, as, e.g., ATCC No. 14899.

Streptomyces nodosus was deposited on Nov. 14, 1962 with the American Type Culture Collection, 10801 University Boulevard, Manassas, Va. 20110–2209. All strains have provided excellent results to date.

Prokaryote protein synthesis is a multistep process that can be inhibited or suppressed at most steps in the synthetic pathway. These steps include, for example, the transcription of mRNA, the binding of mRNA to ribosomes, t-RNA assisted delivery of amino acids and the elongation of the polypeptide strand, among others.

For example, the process of the invention can be conducted with a protein synthesis inhibitor that binds to a 70S and/or 80S ribosome of *Streptomyces nodosus*. Preferably, the process is conducted with a protein synthesis inhibitor that binds to the 70S ribosome of *Streptomyces nodosus*, or to one of the components of the 70S ribosome, e.g., the 16S, 23S, 30S and 50S ribosomal RNA of *Streptomyces nodosus*. Such ribosome binding antibiotics include a number of art-known antibiotics such as the aminoglycosides. These include, e.g., streptomycin, puromycin, dihydrostreptomycin, neomycin, kanamycin, gentamicin, amikacin and tobramycin. Other ribosome-binding antibiotics include the macrolides such as erythromycin, and other antibiotics including the tetracyclines, thiostrepton, chloramphenicol, lincomycin and spectinomycin.

In a more preferred embodiment, *Streptomyces nodosus* can be cultivated with lincomycin or chloramphenicol. In a most preferred embodiment, *Streptomyces nodosus* can be cultivated with chloramphenicol, which has provided the best results of the tested protein synthesis inhibitors.

The time of addition of the protein synthesis inhibitor to the culture of *Streptomyces nodosus* is critical, depending on the compound selected. All inhibitors of 70S ribosome function were active when added in the time period from about 0 to about 24 hours. Some were also effective when added later. It should be realized that with the addition of the inhibitors past about 48 hours, the production of amphotericin A is already underway and the overall yield may be somewhat reduced. A preferred time range for inhibitor addition is from about 0 to 24 hours; and the most preferred time is about at the start of cultivation. Although one may obtain some reduction in amphotericin A production with inhibitor addition past 48 hours, there still will be the problem of removing amphotericin A from amphotericin B.

For convenience, and simply by way of example, the protein inhibitor can be added at one or more of the following times: at about the start of cultivation:, about 24 hours, about 40 hours, about 48 hours and e.g., in a time ranging from about 90 to about 96 hours after commencement of *Streptomyces nodosus* cultivation. The protein synthesis inhibitor can be added once, or for more complete suppression can be added multiple times, e.g., once at from about 0 to about 24 hours and a second time at between about 72 and about 96 hours.

In addition to intermittent addition, in certain aspects the protein synthesis inhibitor may be continuously added or infused into the culture medium, depending upon the type of cultivation process employed. In one aspect, the protein synthesis inhibitor may be premixed at the desired concentration into the cultivation medium, which may be employed for batch, fed batch, semi-continuous or continuous flow cultivation.

The effective concentration of a protein inhibitor is readily determined by cultivating an amphotericin B producing strain with a graded range of protein inhibitor concentrations, monitoring the cell mass and the ratio of amphotericin A and amphotericin B production by, e.g., ultraviolet-visible absorption spectroscopy, or HPLC column chromatography and thereby determining the concentration effective for optimal inhibition of amphotericin A production, without a significant negative effect on cell mass increase or amphotericin B production.

The preferred concentrations of other protein inhibitory antibiotics should be adjusted, for example, relative to the readily determined potency of each such protein synthesis inhibitor in proportion to the potency of chloramphenicol.

The invention is further described in the following examples which are in no way intended to limit the scope of the invention.

EXAMPLE 1

Cultivation of *Streptomyces Nodosus* in the Presence of Protein Inhibitory Antibiotics A. Cultivation of *Streptomyces Nodosus*

The *Streptomyces nodosus* strain IMRU 3694, obtained from the Waksman Institute of Microbiology of Rutgers University was grown in an inoculum medium (YED; see below) and after 4 days the resultant culture was either mixed with 6 ml sterile glycerol (10% v/v glycerol final concentration) and frozen (3 ml portions) and maintained at −20° or used directly as an inoculum for antibiotic production. Inoculum cultures and production fermentations were carried out in 300 ml baffled shake flasks containing either 50 ml of inoculum or production media, respectively.

Yeast Extract Dextrose Medium (YED)

1% yeast extract
1% dextrose
0.1% calcium carbonate in distilled water adjusted to pH 7.2

Production Medium

5% dextrose
1% Bactopeptone
1.0% calcium carbonate
0.001% $MnCl_2.4H_2O$
0.001% $FeSO_4.7H_2O$ in distilled water adjusted to pH 7.2

The flasks, with cotton gauze closures, were sterilized for 15 minutes at 121° C. After inoculation (5 ml), the flasks were maintained at 27° C. with 250 rpm on a rotary shaker.

B. Addition of Protein Synthesis Inhibitory Antibiotics

Figure 1:
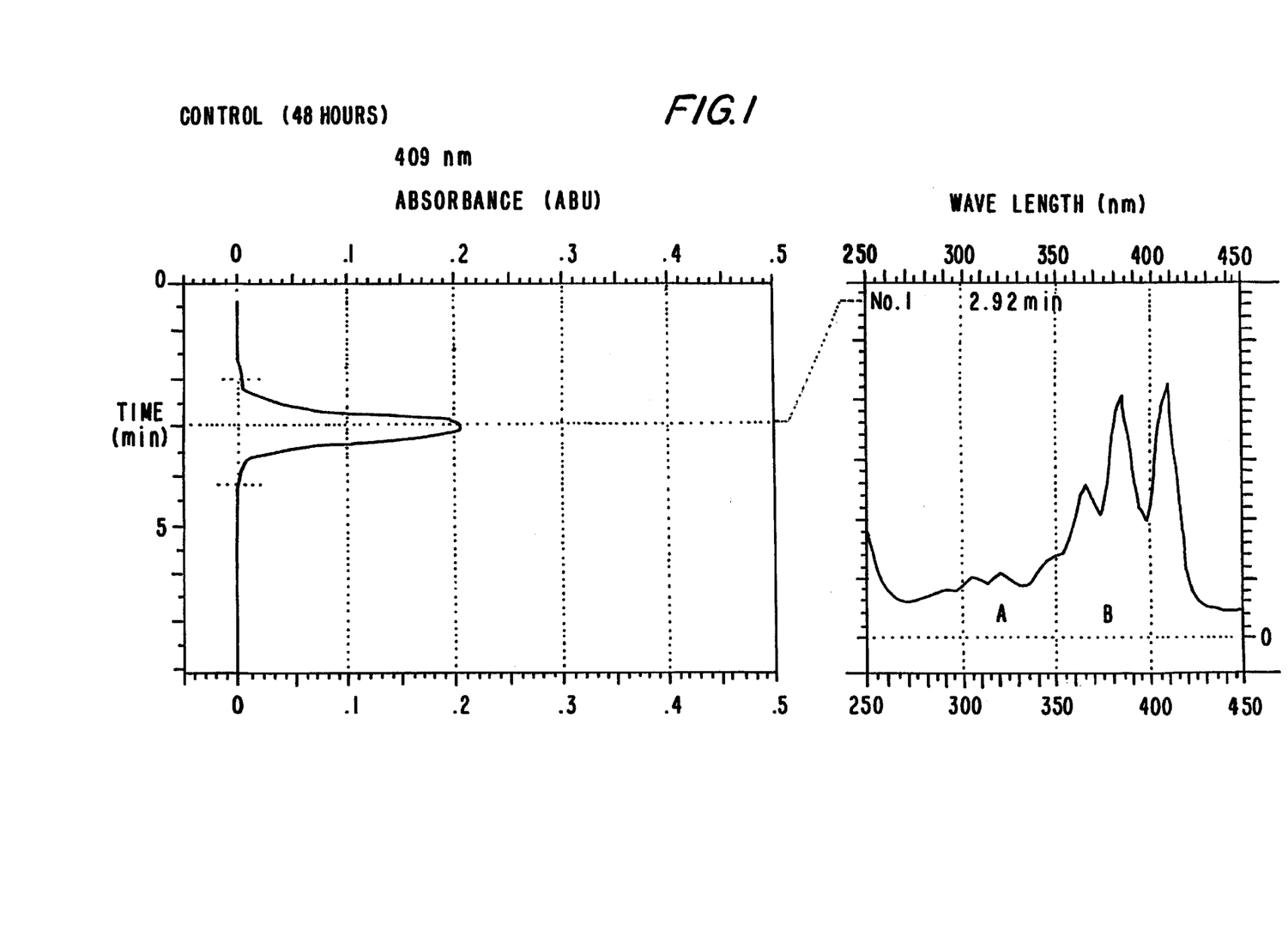
FIG. 1 is a high pressure liquid chromatograph ("HPLC") analysis of a dimethylsulfoxide (DMSO) extract of a control fermentation broth sample taken at 48 hours. "A" indicates the peaks for amphotericin A and "B" indicates the peaks for amphotericin B. The wave lengths of the center peak employed for ultraviolet-visible quantitative measures are 304 nm for amphotericin A and 382 nm for amphotericin B.

The following protein synthesis inhibitors, including chloramphenicol, erythromycin, puromycin, thiostrepton, neomycin, chlortetracycline, streptomycin, lincomycin and dihydrostrepto-mycin were tested. Sterile additions of 20 $\mu$g of antibiotic per 50 ml of production culture medium (0.4 $\mu$g/ml) were made 48 hours after inoculation of the production flasks. At this time, production of both amphotericin A and B was already in progress (FIG. 1). Another addition of the inhibitor (20 $\mu$g) was made after 96 hours of culture. At 192 hours after initiation of the culture growth, or 4 days after the last addition of inhibitor, the fermentation culture was analyzed for the production of amphotericin A and B.

C. Effect of Inhibitors on Cell Culture Growth

To determine the effect of the inhibitors on culture growth, the packed cell volumes were determined by placing 10 ml of the whole culture broth into a 12 ml COREX graduated centrifuge tube. The tubes were then centrifuged for 10 minutes at high speed in a swinging bucket bench top centrifuge. Readings were immediately taken and were expressed directly as ml packed cells per 10 ml total volume.

D. Analysis

Whole culture broth samples were analyzed by mixing 0.5 ml of the culture broth with 4.5 ml dimethylsulfoxide. After vigorous shaking and extraction for 60 minutes, the resultant mixture was centrifuged for 10 minutes at high speed on a bench top centrifuge. The clarified supernatant (0.5 ml) was again diluted with 4.5 ml of methanol and once again centrifuged at high speed for 10 minutes. After passing through a 0.456 $\mu$m syringe filter, the filtrate was subjected to ultraviolet-visible spectroscopic measurements scanning from 450 nm to 250 nm. A portion of the extracts (20 $\mu$l) was used for high performance liquid chromatographic analyses. Where appropriate, dilutions were made to optimize ultraviolet visible-absorption and BPLC procedures.

E. Results

Figure 2:
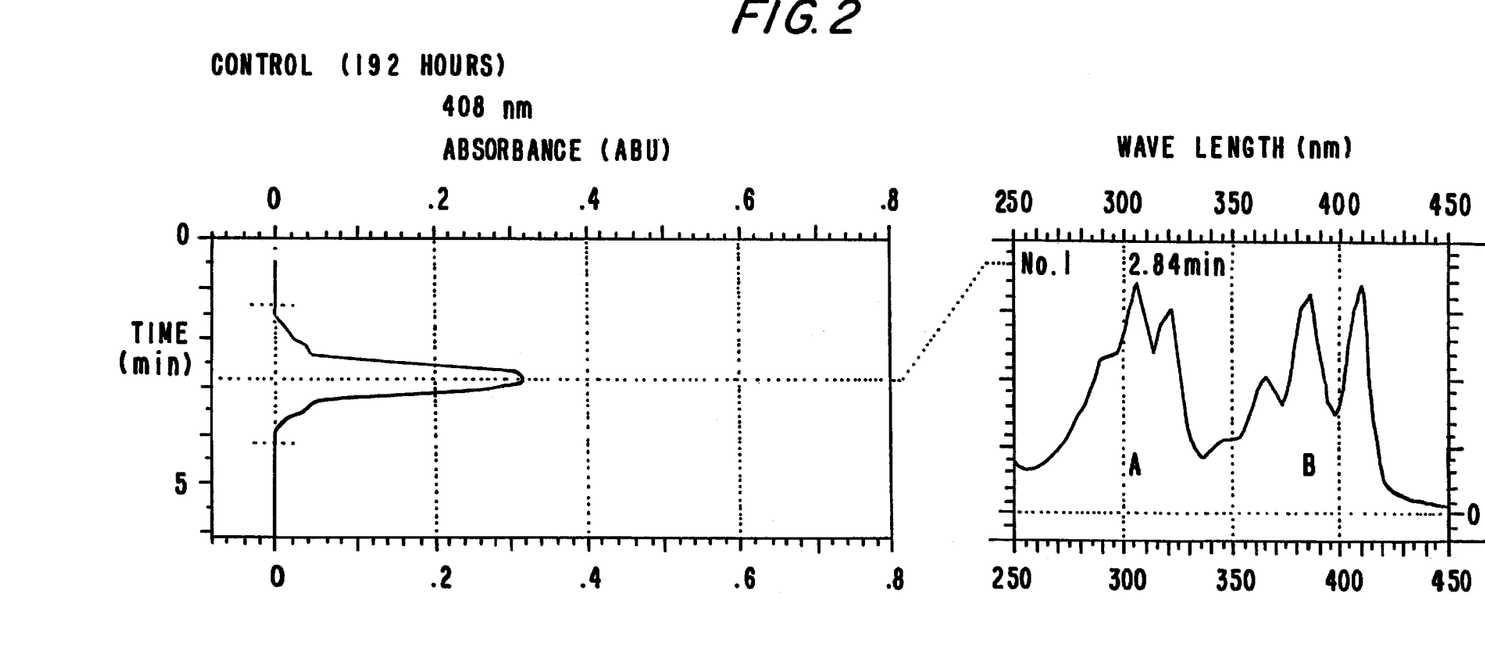
FIG. 2 is a HPLC analysis of a DMSO extract of a control fermentation broth sample taken at 192 hours. "A" indicates the peaks for amphotericin A and "B" indicates the peaks for amphotericin B with ultraviolet-visible spectral analysis.
Figure 3:
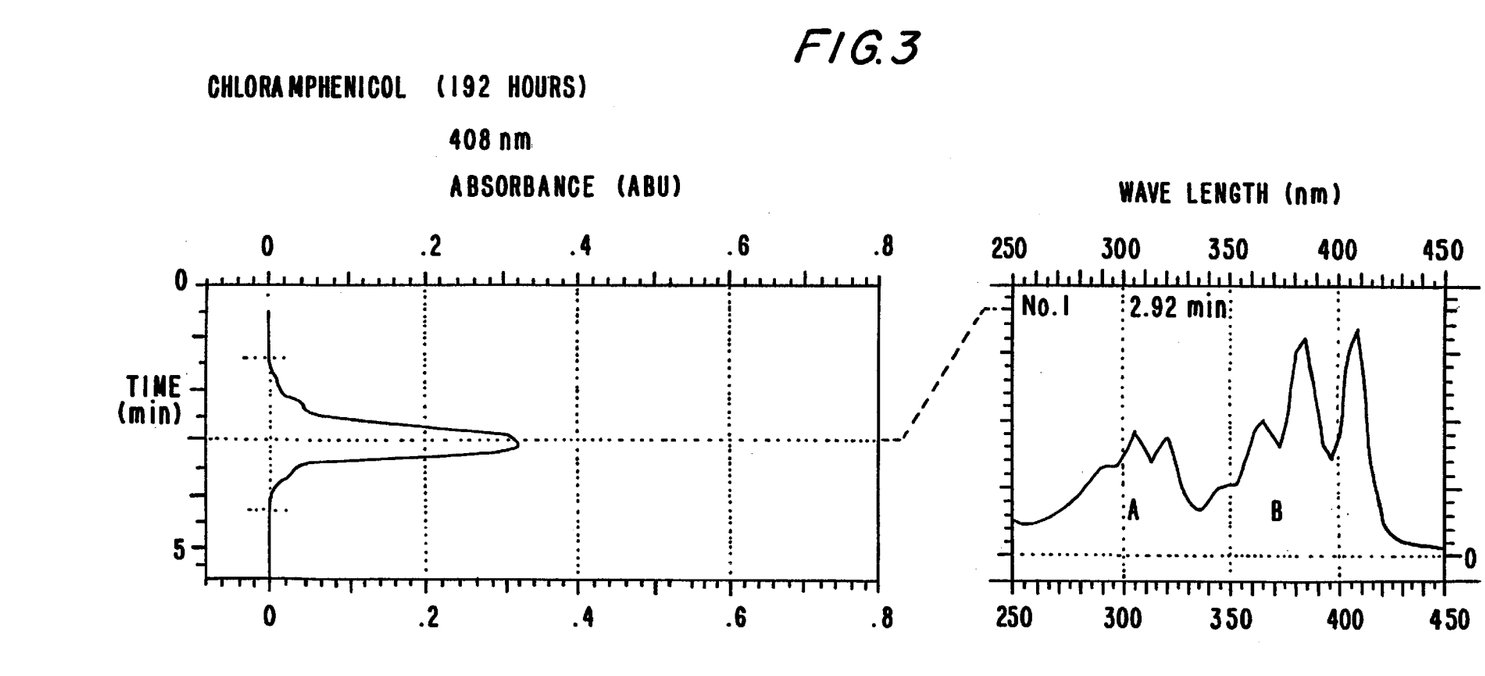
FIG. 3 is a HPLC analysis of a DMSO extract of a fermentation broth sample taken at 192 hours. Two additions of chloramphenicol (0.4 μg/ml, final concentration each) were made at 48 hours and 96 hours. "A" indicates the peaks for amphotericin A and "B" indicates the peaks for amphotericin B with ultraviolet-visible spectral analysis.
Figure 4:
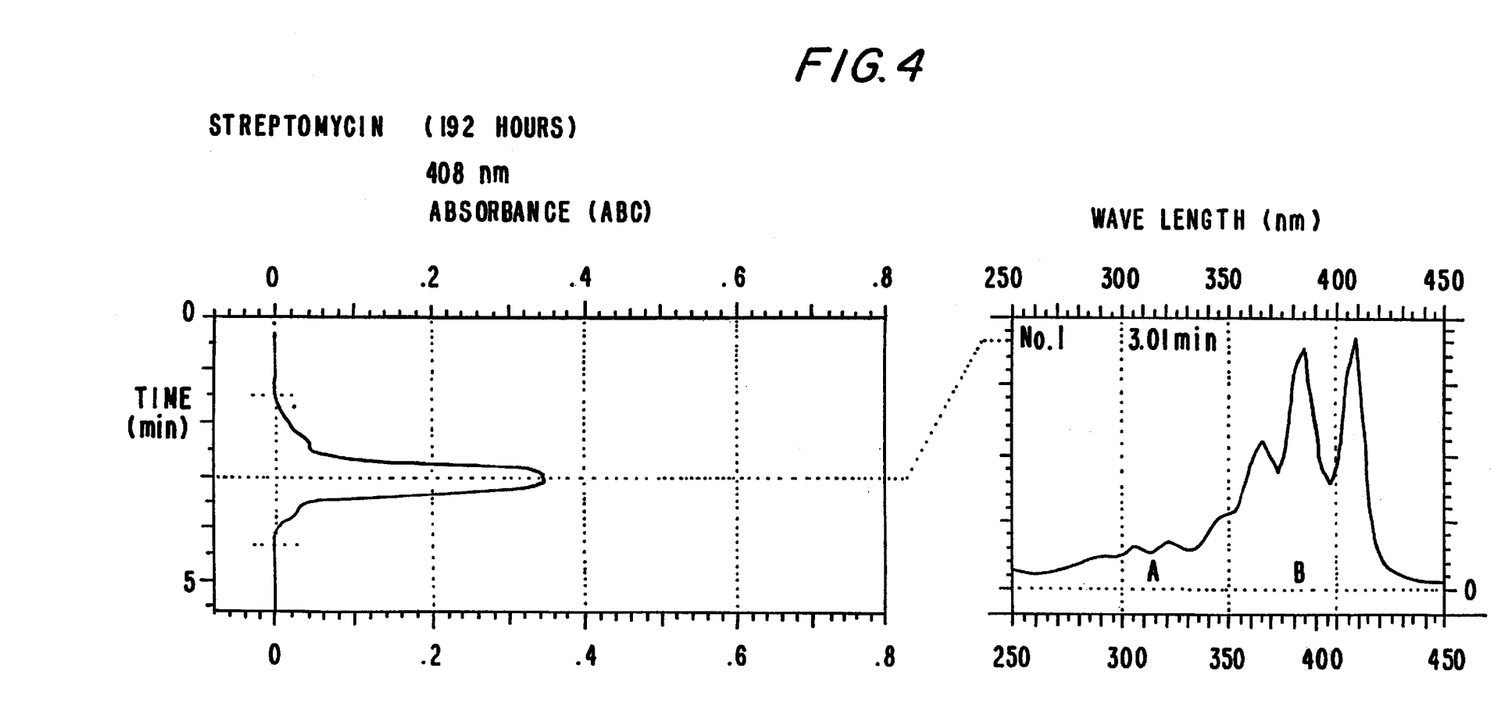
FIG. 4 is a HPLC analysis of a DMSO extract of a fermentation broth sample taken at 192 hours. Two additions of streptomycin) (0.4 μg/ml, final concentration each) were made at 48 hours and 96 hours. "A" indicates the peaks for amphotericin A and "B" indicates the peaks for amphotericin B ultraviolet-visible spectral analysis.
Figure 5:
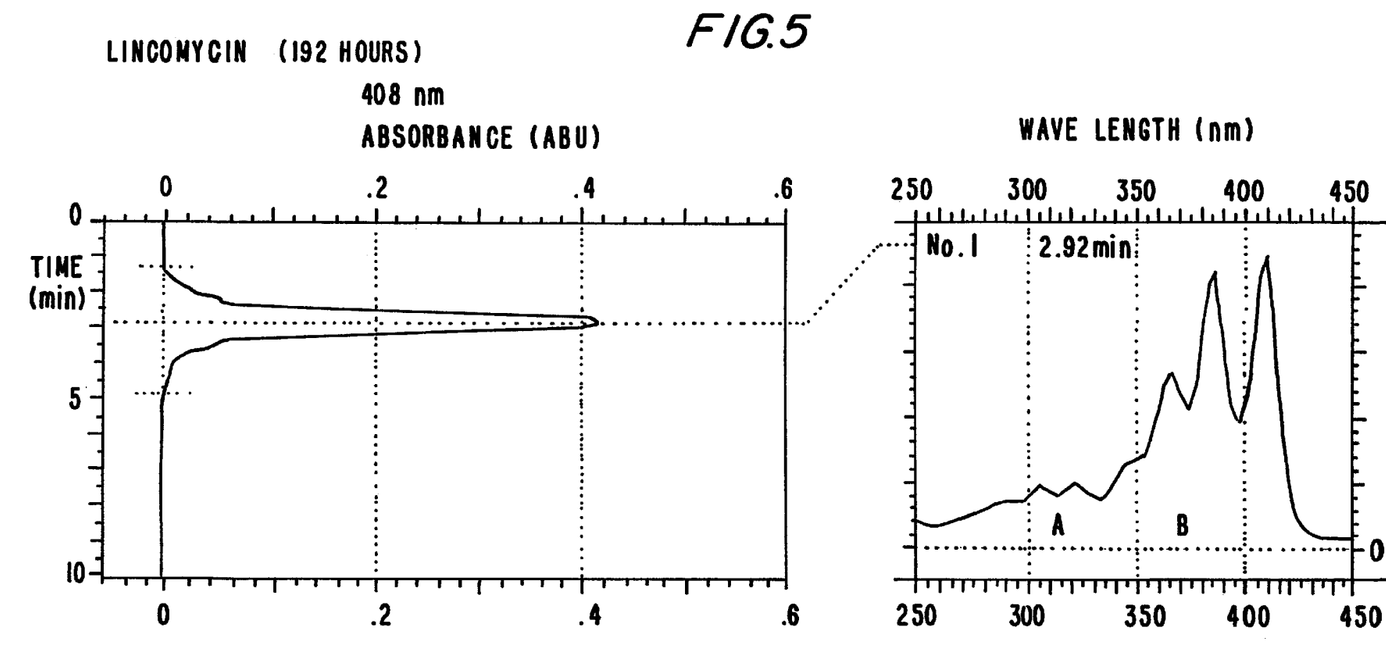
FIG. 5 is a HPLC analysis of a DMSO extract of a fermentation broth sample taken at 192 hours. Two additions of lincomycin (0.4 μg/ml, final concentration each) were made at 48 hours and 96 hours. "A" indicates the peaks for amphotericin A and "B" indicates the peaks for amphotericin B with ultraviolet-visible spectral analysis.

The results of the above experiments with nine protein synthesis inhibitors revealed that amphotericin A production was suppressed by all nine tested compounds relative to untreated controls, as measured by ultraviolet-visible absorption at 192 hours of cultivation. High pressure liquid chromatography ("HPLC") was used to analyze the culture samples. Each resulting HPLC peak was then analyzed by ultraviolet-visible light spectroscopy. For the control, at 48 hours, amphotericin B production dominates (FIG. 1). By 192 hours, the control HPLC peak includes substantial quantities of both amphotericin A and B (FIG. 2). In contrast, when the tested antibiotics were added to the culture medium at 48 hours and again at 96 hours (20 μg/50 ml) at 192 hours, a substantial decrease in amphotericin A production was observed for: chloramphenicol (FIG. 3), streptomycin (FIG. 4), lincomycin (FIG. 5) and thiostrepton (HPLC figure not shown; but see Table 1, below). As can be appreciated from FIG. 4, streptomycin provided the most complete suppression of amphotericin A production at 192 hours.

The quantitative measurements from the HPLC peaks for both amphotericin A and amphotericin B, at 304 and 382 nm at 192 hours are provided by Table 1, below.

TABLE 1

| Treatment | Amphotericin A mg/l | Amphotericin B mg/l |
| --- | --- | --- |
| Control | 2010 | 920 |
| Streptomycin | 325 | 1300 |
| Dihydrostreptomycin | 375 | 1020 |
| Neomycin | 120 | 405 |
| Thiostrepton | 100 | 675 |
| Lincomycin | 400 | 1220 |
| Chloramphenicol | 975 | 1100 |
| Erythromycin | 950 | 1175 |
| Chlortetracycline | 825 | 970 |
| Puromycin | 875 | 950 |

As indicated by Table 1, streptomycin, dihydrostreptomycin, thiostrepton and lincomycin were highly effective in increasing the proportion of amphotericin B produced relative to control. Erythromycin, chlortetracycline, puromycin produced lesser effects on amphotericin A formation. One of the most efficient inhibitors of amphotericin A was lincomycin. The control samples taken at the time (48 hours) that the other experimental groups first received the protein synthesis inhibitors revealed the presence of both amphotericin A and amphotericin B. At the end of the experiment (192 hours), the concentration of amphotericin A in the control broth was significantly higher than amphotericin B.

EXAMPLE 2

24 and 96 Hour Additions

In another experiment, using the methods of Example 1, the protein synthesis inhibitors were added at 24 and 96 hours after inoculation of the production media (50 ml in 300 ml baffled flasks) with inoculum cultures of *Streptomyces nodosus*. In all, 20 μg of each inhibitor was added to each flask after sterile filtration.

After 192 hours of cultivation, the fermentation cultures were subjected to analysis of amphotericin A and B content as described above for Example 1. The results are tabulated below in Table 2.

TABLE 2

| Treatment | Amphotericin A mg/l | Amphotericin B mg/l |
| --- | --- | --- |
| Control | 1975 | 1010 |
| Streptomycin | 175 | 1320 |
| Chloramphenicol | 150 | 1050 |
| Lincomycin | 145 | 1275 |
| Thiostrepton | 220 | 780 |
| Neomycin | 110 | 675 |

Results

As can be appreciated from Table 2, streptomycin and lincomycin provided the best results, both suppressing the production of amphotericin A and increasing the total production of amphotericin B, over the levels measured in the control.

EXAMPLE 3

Determination of Optimal Additions

Additional experiments were carried out with chloramphenicol in order to determine the effects of varying the times of chloramphenicol additions as well as varying the number of additions on amphotericin A production.

A. Methods

Production cultures in 250 ml shake flasks were prepared as described in Example 1, supra. One flask received no treatment and was used as a control. The second flask received 20 μg of chloramphenicol delivered in 1 ml of distilled water at the time of inoculation. The third flask received 20 μg of chloramphenicol 24 hours after inoculation. The fourth flask received 20 μg of chloramphenicol 40 hours after inoculation. The fifth flask received two chloramphenicol treatments. One 20 μg treatment was delivered 24 hours after inoculation and an additional 20 μg treatment 92 hours after inoculation. The 20 μg/ml stock solution of chloramphenicol was prepared from a serial dilution of a 1 mg/ml stock solution. The 20 μg/ml solution was sterile filtered through a 0.22 μm syringe filter.

The control tested the cultivation of *Streptomyces nodosus* with no added protein synthesis inhibitor.

B. Addition at Time Zero

Figure 7:
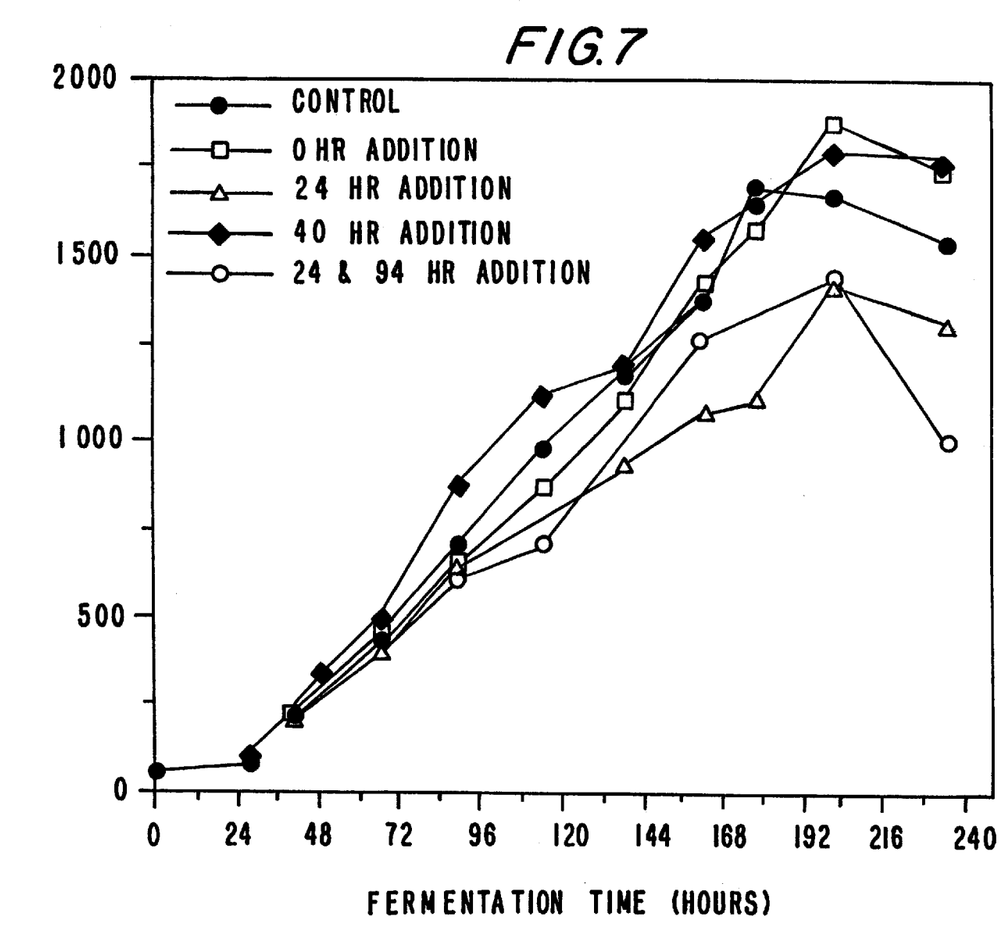
FIG. 7 illustrates spectrophotometric determinations of the production of amphotericin B (mg/l) versus fermentation time for S. nodosus with 0.4 μg/ml of the antibiotic chloramphenicol as the protein inhibitor. The control (●) was cultivated without chloramphenicol, the experimental groups include zero hour addition (□) 24 hour addition (closed triangle), 40 hour addition (closed diamond) and 24 and 94 hour addition (○).
Figure 8:
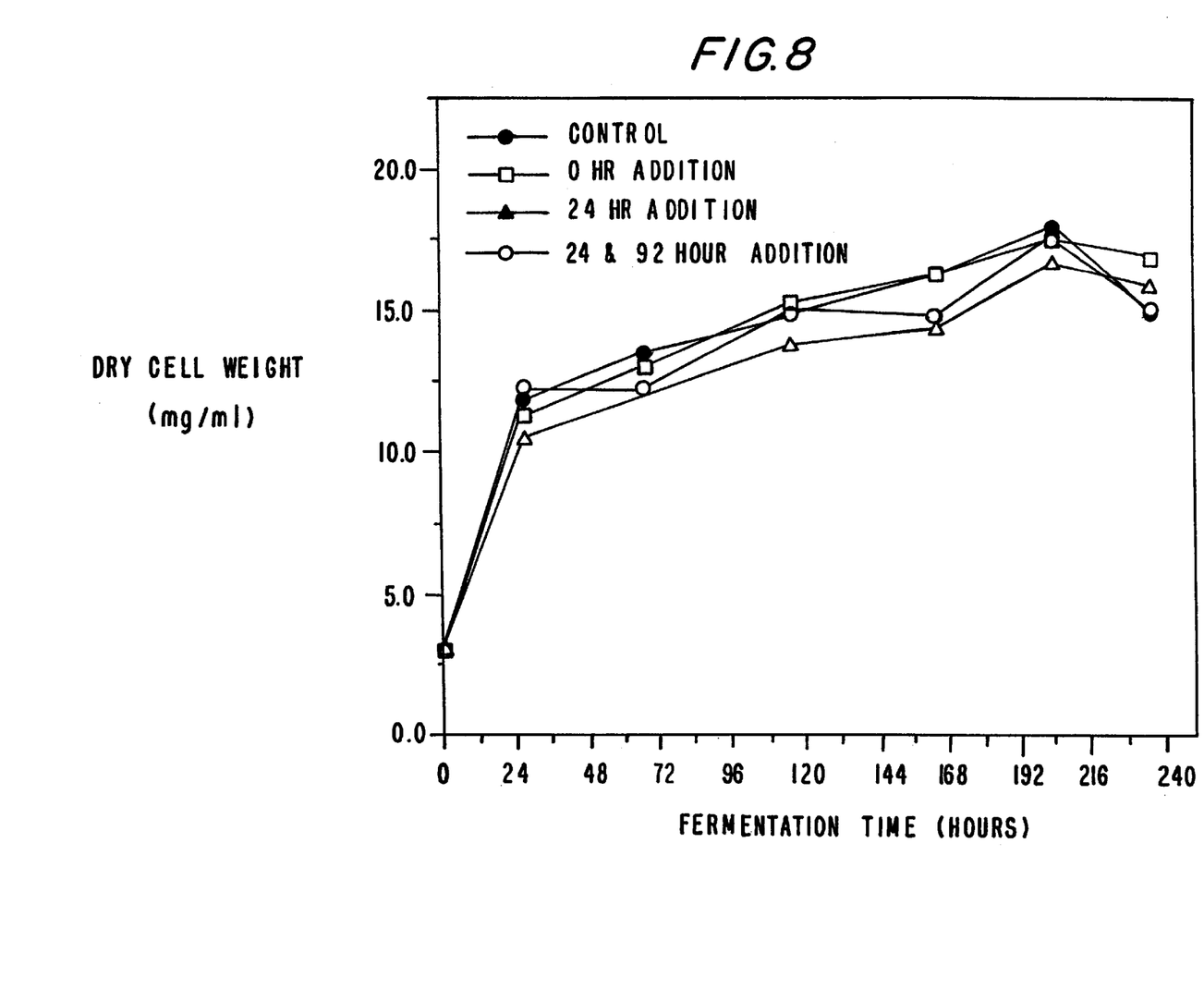
FIG. 8 illustrates dry cell weight (mg/ml) versus fermentation time for S. nodosus with 0.4 μg/ml of the antibiotic chloramphenicol as the protein inhibitor. Dry cell weights were determined by centrifuging 1 ml of culture and weighing the lyophilized pellet. The control (●) was cultivated without chloramphenicol, the experimental groups include zero hour addition (□) 24 hour addition (closed triangle), and 24 and 92 hour addition (○).

Chloramphenicol was added at the time of inoculation (time 0) at a final concentration of 0.4 μg/ml. This addition effectively inhibited the induction of amphotericin A production (FIG. 6, "☐") while not inhibiting the growth of *S. nodosus* as measured by dry cell mass (FIG. 8, as indicated by comparing the dry cell weights (FIG. 8, "☐") with the control (FIG. 8, "closed triangle"). Since production of amphotericin A was delayed by 120 hours, synthesis occurred only during the last 52 hours of the fermentation. Therefore, the amphotericin A level reached 30% that of the control. Amphotericin B production was unaffected (FIG. 7, "○").

C. Addition at 24 Hours

Figure 6:
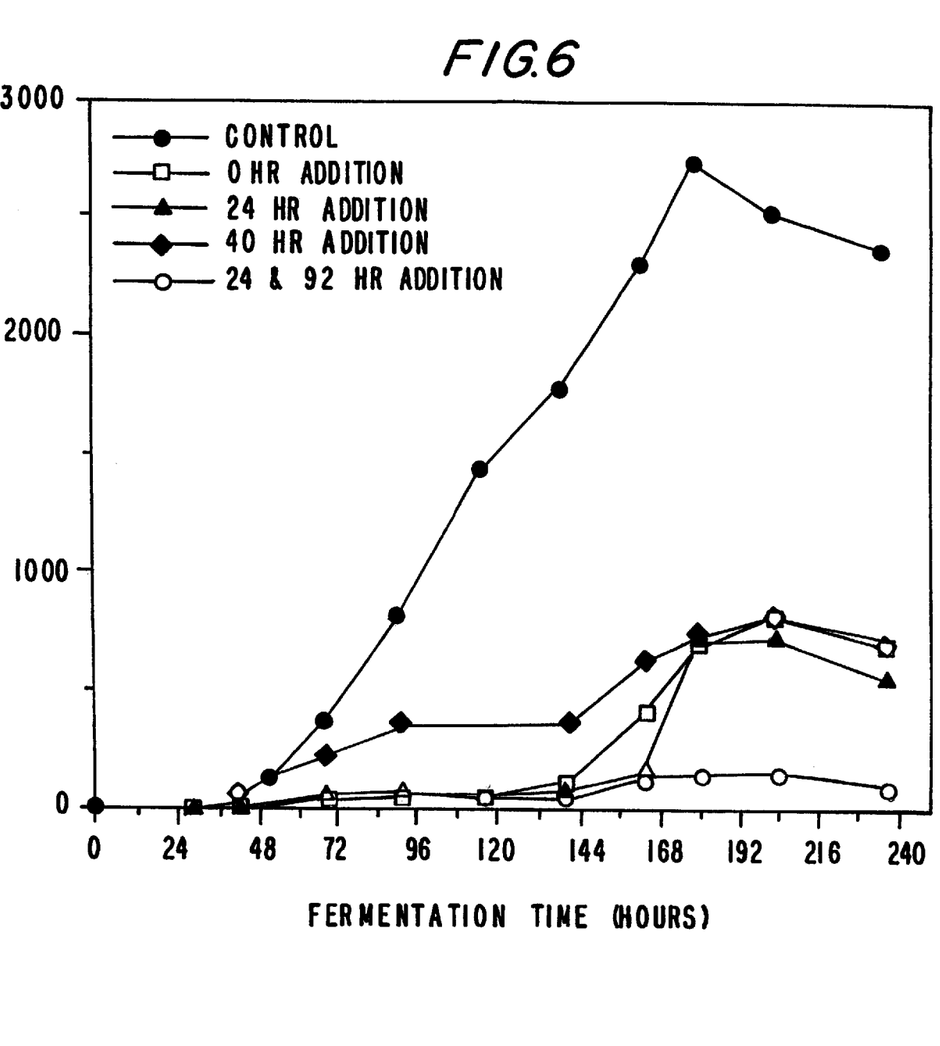
FIG. 6 illustrates spectrophotometric determinations of the production of amphotericin A (mg/l) versus fermentation time for S. nodosus with 0.4 μg/ml of the antibiotic chloramphenicol as the protein inhibitor. Whole culture broth DMSO extracts were diluted in methanol and measured at 305 and 383 nm, respectively. The control (●) was cultivated without chloramphenicol, the experimental groups include zero hour addition (□) 24 hour addition (closed triangle), 40 hour addition (closed diamond) and 24 and 92 hour addition (small closed diamond).

When chloramphenicol was added 24 hours after inoculation, the induction of amphotericin A production was delayed 144 hours from 24 hours to 168 hours (FIG. 6, "closed triangle"). Amphotericin B production was inhibited slightly, but cell growth, as measured by dry cell weight, was not affected (FIG. 8, "closed triangle"). The 24 hours difference in the delay of amphotericin A production between the initial addition and the 24 hour addition suggested that the chloramphenicol was stable for 144 hours. After 144 hours the chloramphenicol activity declined sufficiently to allow resumption of amphotericin A production.

D. Addition at 40 Hours

Chloramphenicol added at 40 hours does not completely inhibit amphotericin A synthesis (FIG. 6, solid diamond). Amphotericin A production continued throughout the fermentation, albeit at a lower rate than that of the control. Amphotericin B production was not inhibited (FIG. 7, solid diamond). Amphotericin A synthesis was began at 24 hours post inoculation. The 40 hour addition of chloramphenicol was 16 hours after the amphotericin A synthesis induction period.

E. Addition at 24 and 92 Hours

When chloramphenicol was added at 24 and 92 hours, amphotericin A production was inhibited throughout the fermentation (FIG. 6, small solid diamond). Amphotericin B synthesis was inhibited slightly (FIG. 7, small solid diamond, but the dry cell weights were unaffected (FIG. 8, "○").

EXAMPLE 4

Effects of Varying Chloramphenicol Concentrations

Different chloramphenicol concentrations were tested. At higher concentrations, amphotericin B production was significantly affected. At lower concentration, the synthesis of amphotericin A production was not completely inhibited.

Discussion

Given the large number of enzymes involved in the synthetic pathway for both amphotericin A and B, the simple introduction of a protein synthesis inhibitor into the culture medium during *Streptomyces nodosus* cultivation would have been expected to disrupt the synthesis of the enzymes necessary for the synthesis of both amphotericin A and B and perhaps other proteins required for cell growth and reproduction.

While the applicants do not wish to be bound by any particular theory or hypothesis as to how the process of the invention operates, it now appears that the primary skeleton of the aglycone ring may be dictated by a discrete number of gene-encoded modules and the individual enzymatic activities that make up each individual module of the polyketide multi-enzyme complex.

The present investigation of the biosynthetic relationship between amphotericin A and B indicates that some intermediates in the formation of amphotericin B serve as a precursors solely for the formation of amphotericin A. The amphotericin antibiotics are structurally related to the large group of macrocyclic polyketides believed to be synthesized by a universal mechanism (polyketide synthesis). The enzymes that catalyze the reactions of the biosynthetic pathway fall into three classes. These include the polyketide multi-enzyme complex (polyketide synthase), the macrolide tailoring enzymes, and finally the glycosylation enzymes. The polyketide synthase catalyzes the head to tail condensation of acetate, propionate, and malonate and/or methyl malonate into a large membered polyoxygenated lactone ring that is referred to herein as an aglycone ring. The tailoring enzymes catalyze the modification of functionality of different chemical moieties on the macrocyclic ring prior of glycosylation by the addition of carbohydrate moieties to the aglycone structure, completing the synthesis of the final product.

If there were two distinct modules encoded by specific microbial genes, one for the synthesis of amphotericin B aglycone and the second for amphotericin A aglycone, then the module coding heptaene synthesis might lack a necessary reductase enzyme that is separately transcribed at a later time interval. Introduction of a low concentration of a protein synthesis inhibitor during *Streptomyces nodosus* cultivation apparently selectively inhibits or suppresses the expression of one or more enzymes necessary for the final reaction step(s) in the production of amphotericin A.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

We claim:

1. A process for producing amphotericin B from *Streptomyces nodosus* while selectively inhibiting co-production of amphotericin A, comprising the steps of:

a) cultivating *Streptomyces nodosus* in a nutrient medium suitable for the production of amphotericin B, said nutrient medium comprising a protein synthesis inhibitor selected from the group consisting of dihydrostreptomycin, neomycin, puromycin, kanamycin, gentamicin, tobramycin, amikacin, lincomycin, thiostrepton, chloramphenicol, spectinomycin, erythromycin and chlortetracycline, said protein synthesis inhibitor in a concentration of from about 0.1 $\mu$g/ml to less than 1.0 $\mu$g/ml, wherein said protein synthesis inhibitor selectively inhibits the co-production of amphotericin A; and b) recovering amphotericin B from the medium.

2. The process of claim 1 wherein said concentration of protein synthesis inhibitor is from about 0.1 $\mu$g/ml to about 0.75 $\mu$g/ml.

3. The process of claim 1 wherein the protein synthesis inhibitor binds to a 70S ribosome of *Streptomyces nodosus*.

4. The process of claim 1 wherein the protein synthesis inhibitor selectively binds to a ribosomal RNA selected from the group consisting of 16S, 23S, 30S and 50S ribosomal RNA of *Streptomyces nodosus*.

5. The process of claim 1 wherein the protein synthesis inhibitor is chloramphenicol.

6. The process of claim 1 wherein the protein synthesis inhibitor is added to the nutrient medium in an initial dose at a time ranging from about 0 to about 100 hours after commencement of *Streptomyces nodosus* cultivation.

7. The process of claim 6 wherein the protein synthesis inhibitor is added to the nutrient medium in an initial dose at a time ranging from about 0 to about 48 hours after commencement of *Streptomyces nodosus* cultivation.

8. The process of claim 7 wherein the protein synthesis inhibitor is added to the nutrient medium in an initial dose at a time ranging from about 0 to about 24 hours after commencement of *Streptomyces nodosus* cultivation.

9. The process of claim 1 wherein said protein synthesis inhibitor is lincomycin.

10. The process of claim 5 wherein said chloramphenicol is present in a concentration of about 0.4 $\mu$g/ml.

* * * * *